US012605476B2

(12) United States Patent
Prince

(10) Patent No.: US 12,605,476 B2
(45) Date of Patent: Apr. 21, 2026

(54) ULTRASOUND GEL-TREATING STATIONS, SYSTEMS, AND METHODS

(71) Applicant: Bard Access Systems, Inc., Salt Lake City, UT (US)

(72) Inventor: Matthew J. Prince, Herriman, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 470 days.

(21) Appl. No.: 18/136,111

(22) Filed: Apr. 18, 2023

(65) Prior Publication Data

US 2024/0350688 A1     Oct. 24, 2024

(51) Int. Cl.
*A61L 2/10*          (2006.01)
*A61L 2/24*          (2006.01)
(Continued)

(52) U.S. Cl.
CPC .................. *A61L 2/10* (2013.01); *A61L 2/24* (2013.01); *A61L 2/26* (2013.01); *A61B 8/4281* (2013.01);
(Continued)

(58) Field of Classification Search
CPC ..... A61L 2/10; A61L 2/24; A61L 2/26; A61L 2202/11; A61L 2202/23; A61B 8/4281
See application file for complete search history.

(56) References Cited

U.S. PATENT DOCUMENTS 5,225,172 A * 7/1993 Meyler ..................... A61L 2/10
                                                                    422/301
5,441,504 A     8/1995 Pohndorf et al.
(Continued)

FOREIGN PATENT DOCUMENTS

CA          2199384 C      6/2006
CA          3080966 A1    11/2020
(Continued)

OTHER PUBLICATIONS

PCT/US2023/083089 filed Dec. 8, 2023, International Search Report and Written Opinion dated Jun. 3, 2024.
(Continued)

*Primary Examiner* — Sean M Luck
(74) *Attorney, Agent, or Firm* — Rutan & Tucker LLP

(57) ABSTRACT

Ultrasound gel-treating stations, systems, and methods enable at least germicidal ultraviolet ("UV")-light treatment of ultrasound gel. For example, an ultrasound gel-treating station can include a housing, a cavity within the housing, and one or more UV-light sources disposed in the cavity or the housing about the cavity. The cavity within the housing can be configured to hold one or more bottles of ultrasound gel. The one-or-more UV-light sources can be configured for irradiating the one-or-more bottles of ultrasound gel with germicidal radiation when the one-or-more bottles of ultrasound gel are disposed in the cavity. Heat dissipated by the one-or-more UV-light sources can warm the one-or-more bottles of ultrasound gel. Additionally or alternatively, the ultrasound gel-treating station can further include one or more heating elements disposed in the cavity or the housing about the cavity for warming the one-or-more bottles of ultrasound gel.

25 Claims, 5 Drawing Sheets

Figure 1:
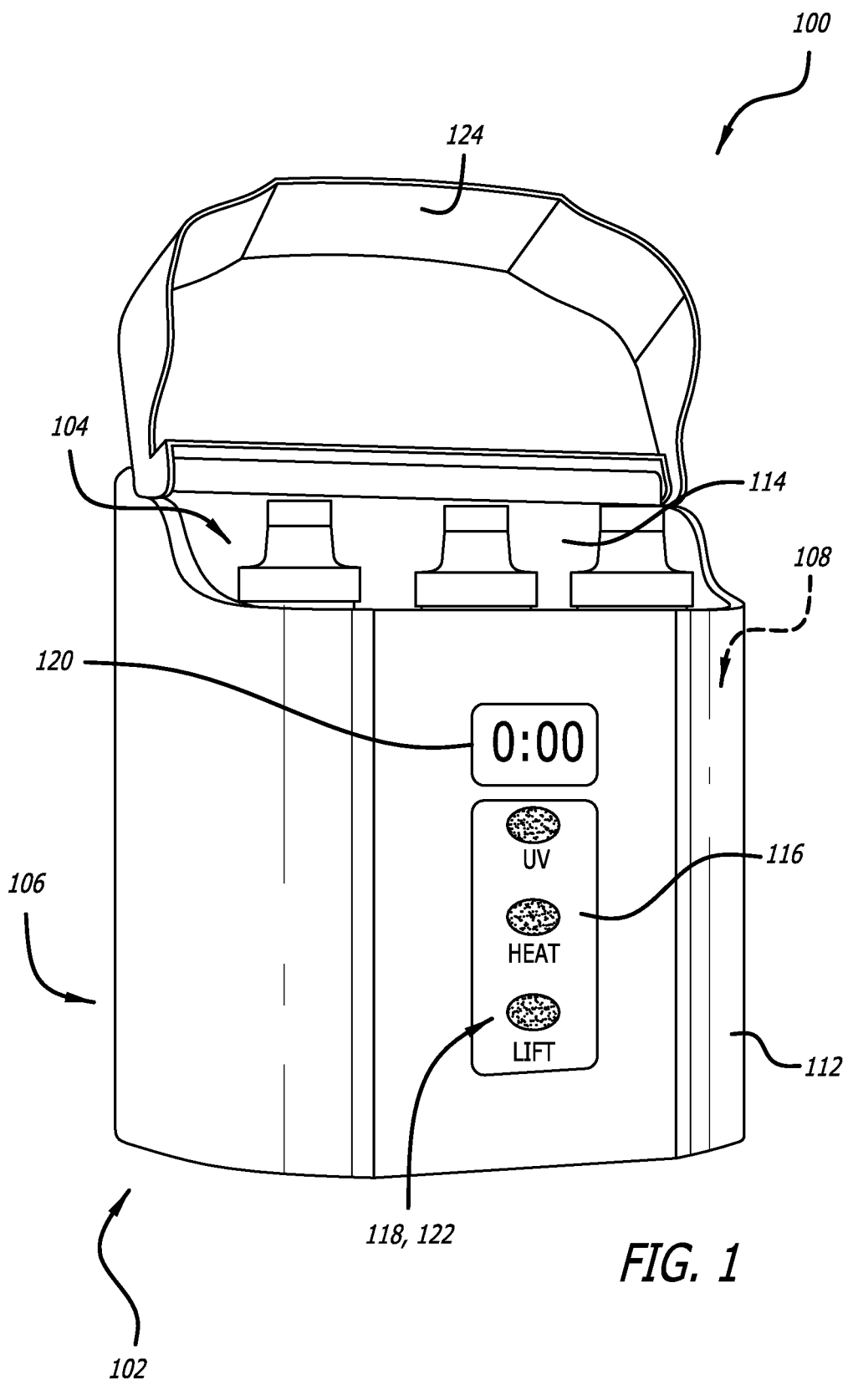

(51) Int. Cl.
*A61L 2/26* (2006.01)
*A61B 8/00* (2006.01)

(52) U.S. Cl.
CPC ........ *A61L 2202/11* (2013.01); *A61L 2202/23* (2013.01)

(56) References Cited

U.S. PATENT DOCUMENTS

| | | |
|---|---|---|
| 6,811,563 B2 | 11/2004 | Savage, Jr. et al. |
| 6,908,460 B2 | 6/2005 | DiStefano |
| 7,274,844 B2 | 9/2007 | Walt et al. |
| 8,197,087 B2 | 6/2012 | Sobue et al. |
| 8,246,666 B2 | 8/2012 | Pressler et al. |
| 8,372,128 B2 | 2/2013 | Reuben |
| 8,387,405 B2 | 3/2013 | Johnson |
| 8,556,950 B2 | 10/2013 | Rioux et al. |
| 9,592,374 B2 | 3/2017 | Muse |
| 9,604,072 B2 | 3/2017 | Brezinski |
| 9,925,285 B1 | 3/2018 | Zaborsky et al. |
| 9,981,052 B2 | 5/2018 | Clynne et al. |
| 10,603,393 B2 | 3/2020 | Rioux et al. |
| 10,639,389 B2 | 5/2020 | Paul et al. |
| 2002/0081228 A1 | 6/2002 | Hui et al. |
| 2003/0018373 A1 | 1/2003 | Eckhardt et al. |
| 2003/0036735 A1 | 2/2003 | Jepson et al. |
| 2003/0063997 A1 | 4/2003 | Fryer et al. |
| 2005/0101854 A1* | 5/2005 | Larson .................... A61L 2/10 600/407 |
| 2007/0123825 A1 | 5/2007 | King et al. |
| 2008/0027399 A1 | 1/2008 | Harding et al. |
| 2008/0257355 A1 | 10/2008 | Rao et al. |
| 2008/0283769 A1 | 11/2008 | Deshays |
| 2009/0177163 A1 | 7/2009 | King et al. |
| 2010/0296971 A1 | 11/2010 | Gaska et al. |
| 2011/0144566 A1 | 6/2011 | Dacey, Jr. et al. |
| 2012/0116294 A1 | 5/2012 | Boenig et al. |
| 2012/0143138 A1 | 6/2012 | King et al. |
| 2012/0161032 A1 | 6/2012 | Arcand et al. |
| 2012/0321509 A1 | 12/2012 | Bak |
| 2013/0303996 A1 | 11/2013 | Rasooly et al. |
| 2013/0323119 A1 | 12/2013 | Alwan |
| 2013/0323120 A1 | 12/2013 | Ma |
| 2014/0217307 A1 | 8/2014 | Messina et al. |
| 2014/0257186 A1 | 9/2014 | Kerr |
| 2015/0080851 A1 | 3/2015 | Kurth et al. |
| 2015/0148734 A1 | 5/2015 | Fewkes et al. |
| 2015/0157209 A1 | 6/2015 | Dantus |
| 2015/0165185 A1 | 6/2015 | Cohen et al. |
| 2015/0217010 A1 | 8/2015 | Whitney |
| 2015/0231287 A1 | 8/2015 | Lin et al. |
| 2015/0238273 A1 | 8/2015 | Russo |
| 2015/0245810 A1* | 9/2015 | Shine .................... A61B 8/44 222/105 |
| 2015/0273093 A1 | 10/2015 | Holub et al. |
| 2015/0283277 A1 | 10/2015 | Schafer et al. |
| 2016/0038621 A1 | 2/2016 | Victor et al. |
| 2016/0128526 A1 | 5/2016 | Dobrinsky et al. |
| 2016/0151639 A1 | 6/2016 | Scharf et al. |
| 2016/0303265 A1* | 10/2016 | Coles .................... A61L 2/24 |
| 2016/0310077 A1 | 10/2016 | Hunter et al. |
| 2016/0317687 A1 | 11/2016 | Dayton |
| 2017/0136209 A1 | 5/2017 | Burnett et al. |
| 2017/0196478 A1 | 7/2017 | Hunter |
| 2017/0232123 A1 | 8/2017 | Burapachaisri et al. |
| 2017/0252550 A1 | 9/2017 | Wegener et al. |
| 2017/0281812 A1 | 10/2017 | Dobrinsky et al. |
| 2017/0296142 A1 | 10/2017 | Wodecki et al. |
| 2018/0280616 A1 | 10/2018 | Witt et al. |
| 2018/0369560 A1 | 12/2018 | Ball et al. |
| 2019/0111240 A1 | 4/2019 | Fia et al. |
| 2019/0151587 A1 | 5/2019 | Vazales et al. |
| 2019/0192872 A1 | 6/2019 | Schwarz et al. |
| 2019/0290360 A1 | 9/2019 | Goodrich et al. |
| 2019/0290791 A1 | 9/2019 | Baker et al. |
| 2019/0374668 A1 | 12/2019 | Kopperschmidt et al. |
| 2020/0030473 A1 | 1/2020 | Sugimoto et al. |
| 2020/0147248 A1 | 5/2020 | Mintie et al. |
| 2020/0188543 A1 | 6/2020 | Etter et al. |
| 2020/0261610 A1 | 8/2020 | Rioux et al. |
| 2020/0324078 A1 | 10/2020 | Motley et al. |
| 2020/0360549 A1 | 11/2020 | Neveu et al. |
| 2020/0368379 A1 | 11/2020 | Agarwal |
| 2021/0113725 A1 | 4/2021 | Etter et al. |
| 2021/0154342 A1 | 5/2021 | Canfield |
| 2021/0162081 A1 | 6/2021 | Zhang et al. |
| 2021/0204818 A1 | 7/2021 | Akins et al. |
| 2021/0236859 A1 | 8/2021 | Park et al. |
| 2021/0338879 A1 | 11/2021 | Davis et al. |
| 2022/0016439 A1 | 1/2022 | Shah et al. |
| 2022/0152243 A1 | 5/2022 | Koppen et al. |
| 2022/0203007 A1 | 6/2022 | Yuds et al. |
| 2022/0273837 A1 | 9/2022 | Paul et al. |
| 2022/0313851 A1 | 10/2022 | Subramanya et al. |
| 2022/0347456 A1 | 11/2022 | Messerly |
| 2022/0387643 A1 | 12/2022 | Baarman |
| 2023/0118324 A1 | 4/2023 | Hong et al. |
| 2023/0233716 A1 | 7/2023 | Yoon et al. |
| 2023/0293741 A1 | 9/2023 | Matsui et al. |
| 2023/0301626 A1 | 9/2023 | Howell |
| 2024/0115749 A1 | 4/2024 | Payne et al. |
| 2024/0188859 A1 | 6/2024 | Fellner et al. |
| 2024/0189467 A1 | 6/2024 | Urry et al. |
| 2024/0226350 A1 | 7/2024 | Payne et al. |
| 2024/0226351 A1 | 7/2024 | Payne et al. |
| 2024/0226352 A1 | 7/2024 | Fellner et al. |
| 2024/0252789 A1 | 8/2024 | Hayden et al. |
| 2024/0335636 A1 | 10/2024 | Laine et al. |
| 2024/0342325 A1 | 10/2024 | Urry et al. |
| 2024/0374770 A1 | 11/2024 | Durfee |
| 2025/0073360 A1 | 3/2025 | Payne et al. |

FOREIGN PATENT DOCUMENTS

| | | |
|---|---|---|
| CN | 104873219 A | 9/2015 |
| CN | 106308727 A | 1/2017 |
| CN | 208481489 U | 2/2019 |
| CN | 209790441 U | 12/2019 |
| CN | 213373944 U | 6/2021 |
| CN | 213551294 U | 6/2021 |
| CN | 113101207 A | 7/2021 |
| CN | 213642120 U | 7/2021 |
| CN | 113476076 A | 10/2021 |
| CN | 215426269 U | 1/2022 |
| EP | 3195805 A1 | 7/2017 |
| EP | 3738617 A2 | 11/2020 |
| JP | 2005198761 A | 7/2005 |
| KR | 20140003473 U | 6/2014 |
| KR | 101654328 B1 | 9/2016 |
| KR | 20220000634 U | 3/2022 |
| KR | 20220063891 A | 5/2022 |
| KR | 102452057 B1 | 10/2022 |
| WO | 9607451 A2 | 3/1996 |
| WO | 2011068545 A1 | 6/2011 |
| WO | 2013134421 A1 | 9/2013 |
| WO | 2014165854 A1 | 10/2014 |
| WO | 2015157518 A1 | 10/2015 |
| WO | 2019108431 A1 | 6/2019 |
| WO | 2020115230 A1 | 6/2020 |
| WO | 2021146701 A1 | 7/2021 |
| WO | 2021157769 A1 | 8/2021 |
| WO | 2022036886 A1 | 2/2022 |
| WO | 2022046138 A1 | 3/2022 |
| WO | 2022200038 A2 | 9/2022 |
| WO | 2022252479 A1 | 11/2022 |
| WO | 2023183426 A1 | 9/2023 |
| WO | 2024081335 A1 | 4/2024 |
| WO | 2024124112 A1 | 6/2024 |
| WO | 2024129817 A1 | 6/2024 |
| WO | 2024151420 A1 | 7/2024 |
| WO | 2024/151421 A1 | 7/2024 |
| WO | 2024/151648 A1 | 7/2024 |
| WO | 2024163670 A1 | 8/2024 |
| WO | 2024211387 A1 | 10/2024 |
| WO | 2024215932 A1 | 10/2024 |

(56)          References Cited

FOREIGN PATENT DOCUMENTS

WO          2024220523  A1    10/2024
WO          2024233805  A1    11/2024
WO          2025049496  A1     3/2025

OTHER PUBLICATIONS

PCT/US2023/085839 filed Dec. 22, 2023, International Search Report and Written Opinion dated Jun. 11, 2024.
PCT/US2024/013858 filed Jan. 31, 2024, International Search Report and Written Opinion dated May 22, 2024.
PCT/US2023/015961 filed Mar. 22, 2023, International Search Report and Written Opinion dated Jul. 17, 2023.
PCT/US2023/034981 filed Oct. 11, 2023, International Search Report and Written Opinion dated Dec. 11, 2023.
PCT/US2024/024136 filed Apr. 11, 2024, International Search Report and Written Opinion dated Sep. 18, 2024.
PCT/US2024/024969 filed Apr. 17, 2024, International Search Report and Written Opinion dated Sep. 27, 2024.
PCT/US2024/028630 filed May 9, 2024, International Search Report and Written Opinion dated Sep. 18, 2024.
CS Medical "Caring for TEE Probes the Right Way" Mar. 17, 2022.
PCT/US2023/085837 filed Dec. 22, 2023, International Preliminary Report on Patentability dated Jul. 3, 2025.
PCT/US2024/013858 filed Jan. 31, 2024 International Preliminary Report on Patentability dated Jul. 31, 2025.
PCT/US2024/022801 filed Apr. 4, 2024, International Search Report and Written Opinion dated Sep. 6, 2024.
U.S. Appl. No. 17/732,614, filed Apr. 29, 2022 Final Office Action dated Sep. 4, 2025.
U.S. Appl. No. 17/963,594, filed Oct. 11, 2022 Non-Final Office Action dated Aug. 22, 2025.
U.S. Appl. No. 18/077,994, filed Dec. 8, 2022 Non-Final Office Action dated Jul. 30, 2025.
U.S. Appl. No. 18/080,624, filed Dec. 13, 2022 Non-Final Office Action dated Oct. 1, 2025.
U.S. Appl. No. 18/080,624, filed Dec. 13, 2022 Restriction Requirement dated Jul. 10, 2025.
U.S. Appl. No. 18/094,760, filed Jan. 9, 2023 Non-Final Office Action dated Sep. 10, 2025.
U.S. Appl. No. 18/094,760, filed Jan. 9, 2023 Restriction Requirement dated Jun. 18, 2025.
U.S. Appl. No. 18/094,785, filed Jan. 9, 2023 Non-Final Office Action dated Aug. 27, 2025.
U.S. Appl. No. 18/094,785, filed Jan. 9, 2023 Restriction Requirement dated Jun. 18, 2025.
U.S. Appl. No. 18/095,469, filed Jan. 10, 2023 Non-Final Office Action dated Sep. 8, 2025.
U.S. Appl. No. 18/195,018, filed May 9, 2023 Non-Final Office Action dated Jul. 3, 2025.
PCT/US2024/044069 filed Aug. 27, 2024, International Search Report and Written Opinion dated Jan. 31, 2025.
U.S. Appl. No. 17/732,614, filed Apr. 29, 2022 Non-Final Office Action dated May 9, 2025.
U.S. Appl. No. 17/963,594, filed Oct. 11, 2022 Restriction Requirement dated Jun. 3, 2025.
U.S. Appl. No. 18/125,029, filed Mar. 22, 2023 Notice of Allowance dated Dec. 18, 2024.
PCT/US2023/083767 filed Dec. 13, 2023, International Search Report and Written Opinion dated Apr. 25, 2024.
PCT/US2023/085837 filed Dec. 22, 2023, International Search Report and Written Opinion dated Apr. 9, 2024.
PCT/US2024/010902 filed Jan. 9, 2024, International Search Report and Written Opinion dated Apr. 24, 2024.
Cabral, João, and Rodrigues A. G. "Blue light disinfection in hospital infection control: advantages, drawbacks, and pitfalls." Antibiotics 8.2 (2019): 58.
Changtong et al., "A porphyrin molecule that generates, traps, stores, and releases singlet oxygen.", Journal of Photochemistry and Photobiology A: Chemistry 260 (Sep. 13, 2013).
Halstead, Fenella D., et al. "The potential of visible blue light (405 nm) as a novel decontamination strategy for carbapenemase-producing enterobacteriaceae (CPE)." Antimicrobial Resistance & Infection Control 8.1 (2019): 1-8.
PCT/US2022/026888 filed Apr. 29, 2022 International Search Report and Writtent Opinion dated Jul. 29, 2022.
Tsen et al., "Inactivation of multidrug-resistant bacteria and bacterial spores and generation of high-potency bacterial vaccines using ultrashort pulsed lasers." Journal of Biophotonics, 2021.
U.S. Appl. No. 17/732,614, filed Apr. 29, 2022 Non-Final Office Action dated Jan. 28, 2026.
U.S. Appl. No. 18/080,624, filed Dec. 13, 2022 Final Office Action dated Jan. 30, 2026.
U.S. Appl. No. 18/132,261, filed Apr. 7, 2023 Non-Final Office Action dated Feb. 9, 2026.

* cited by examiner

ULTRASOUND GEL-TREATING STATIONS, SYSTEMS, AND METHODS

BACKGROUND

Ultrasound gel warmers exist, but existing ultrasound gel warmers can promote bacterial growth and, therefore, be a source of infection. As such, it is not advisable to use the existing ultrasound gel warmers in sterile procedures such as those for placing percutaneous catheters. Use of packets of sterile ultrasound gel, which packets can be warmed in ultrasound gel warmers configured therefor, offer a work-around for providing warm, sterile ultrasound gel for the foregoing sterile procedures, but the packets of sterile ultrasound gel are not as economical as bottles of ultrasound gel. That, and the packets of sterile ultrasound gel produce more waste than the bottles of ultrasound gel.

Disclosed herein are ultrasound gel-treating stations, systems, and methods that address the foregoing.

SUMMARY

Disclosed herein is an ultrasound gel-treating station including, in some embodiments, a housing, a cavity within the housing, one or more heating elements disposed in the cavity or the housing about the cavity, and one or more ultraviolet ("UV")-light sources disposed in the cavity or the housing. The cavity within the housing is configured to hold one or more bottles of ultrasound gel. The one-or-more heating elements are configured for warming the one-or-more bottles of ultrasound gel when the one-or-more bottles of ultrasound gel are disposed in the cavity. The one-or-more UV-light sources are configured for irradiating the one-or-more bottles of ultrasound gel with germicidal radiation when the one-or-more bottles of ultrasound gel are disposed in the cavity.

In some embodiments, the ultrasound gel-treating station further includes a cover for covering the cavity when at least the one-or-more bottles of ultrasound gel are disposed in the cavity and being warmed, irradiated, or both warmed and irradiated.

In some embodiments, the ultrasound gel-treating station is configured to stop irradiating the one-or-more bottles of ultrasound gel when the cavity is uncovered.

In some embodiments, the ultrasound gel-treating station further includes a microcontroller configured for operating the ultrasound gel-treating station. The microcontroller is disposed within the housing with a sensor module including one or more sensors configured to sense conditions in the cavity for starting, stopping, or adjusting the one-or-more heating elements or the one-or-more UV-light sources.

In some embodiments, the microcontroller is further coupled to one or more visual indicators disposed in the housing for indicating when the one-or-more bottles of ultrasound gel are being warmed, irradiated, both warmed and irradiated, or subsequent thereto.

In some embodiments, the microcontroller is further coupled to a timer disposed in the housing for indicating when the one-or-more bottles of ultrasound gel will be warm, disinfected, or both warmed and disinfected.

In some embodiments, the ultrasound gel-treating station further includes an actuator disposed in the housing for lifting the one-or-more bottles of ultrasound gel at least partially out of the ultrasound gel-treating station.

In some embodiments, the ultrasound gel-treating station is integrated into a roll stand or cart.

Also disclosed herein is an ultrasound gel-treating station including, in some embodiments, a housing, a cavity within the housing, and one or more UV-light sources disposed in the cavity or the housing about the cavity. The cavity within the housing is configured to hold one or more bottles of ultrasound gel. The one-or-more UV-light sources are configured for irradiating the one-or-more bottles of ultrasound gel with germicidal radiation when the one-or-more bottles of ultrasound gel are disposed in the cavity.

In some embodiments, heat dissipated by the one-or-more UV-light sources warms the one-or-more bottles of ultrasound gel when the one-or-more bottles of ultrasound gel are disposed in the cavity.

In some embodiments, the ultrasound gel-treating station further includes a cover for covering the cavity when at least the one-or-more bottles of ultrasound gel are disposed in the cavity and being irradiated.

In some embodiments, the ultrasound gel-treating station is configured to stop irradiating the one-or-more bottles of ultrasound gel when the cavity is uncovered.

In some embodiments, the ultrasound gel-treating station further includes a microcontroller configured for operating the ultrasound gel-treating station. The microcontroller is disposed within the housing with a sensor module including one or more sensors configured to sense conditions in the cavity for starting, stopping, or adjusting the one-or-more UV-light sources.

In some embodiments, the microcontroller is further coupled to one or more visual indicators disposed in the housing for indicating when the one-or-more bottles of ultrasound gel are being irradiated.

In some embodiments, the microcontroller is further coupled to a timer disposed in the housing for indicating when the one-or-more bottles of ultrasound gel will be disinfected.

In some embodiments, the ultrasound gel-treating station further includes an actuator disposed in the housing for lifting the one-or-more bottles of ultrasound gel at least partially out of the ultrasound gel-treating station.

Also disclosed herein is an ultrasound gel-treating system including, in some embodiments, one or more bottles of ultrasound gel and an ultrasound gel-treating station. Each bottle of the one-or-more bottles is formed of a pliable polymeric material sufficiently transparent to transmit UV light therethrough. The ultrasound gel-treating station includes a housing, a cavity within the housing, and one or more UV-light sources disposed in the cavity or the housing about the cavity. The cavity within the housing is configured to hold the one-or-more bottles of ultrasound gel. The one-or-more UV-light sources are configured for irradiating the one-or-more bottles of ultrasound gel with germicidal radiation when the one-or-more bottles of ultrasound gel are disposed in the cavity.

In some embodiments, the ultrasound gel-treating station further includes one or more heating elements disposed in the cavity or the housing about the cavity for warming the one-or-more bottles of ultrasound gel when the one-or-more bottles of ultrasound gel are disposed in the cavity.

In some embodiments, heat dissipated by the one-or-more UV-light sources warms the one-or-more bottles of ultrasound gel when the one-or-more bottles of ultrasound gel are disposed in the cavity.

In some embodiments, the ultrasound gel-treating station further includes a cover for covering the cavity when at least the one-or-more bottles of ultrasound gel are disposed in the cavity and being irradiated.

In some embodiments, the ultrasound gel-treating station is configured to stop irradiating the one-or-more bottles of ultrasound gel when the cavity is uncovered.

In some embodiments, the ultrasound gel-treating station further includes a microcontroller configured for operating the ultrasound gel-treating station. The microcontroller is disposed within the housing with a sensor module including one or more sensors configured to sense conditions in the cavity for starting, stopping, or adjusting the one-or-more UV-light sources.

In some embodiments, the ultrasound gel-treating station further includes an actuator disposed in the housing for lifting the one-or-more bottles of ultrasound gel at least partially out of the ultrasound gel-treating station.

In some embodiments, the germicidal radiation is selected from broad spectrum UV-visible light, broad spectrum UV light, UVA light, UVB light, UVC light, blue light, and modulated light thereof, wherein the modulated light is modulated with respect to frequency, power, duration, or a combination thereof.

In some embodiments, the polymeric material of which the one-or-more bottles are formed is selected from a polycarbonate, a polyethylene terephthalate, a polyvinyl chloride, a polyurethane, a poly (methyl methacrylate), a polyimide, a polyetherimide, and a cyclic olefin polymer, the polymeric material optionally including one or more comonomer residues, one or more plasticizers, or a combination thereof.

These and other features of the concepts provided herein will become more apparent to those of skill in the art in view of the accompanying drawings and following description, which describe particular embodiments of such concepts in greater detail.

DRAWINGS

FIG. 1 illustrates an ultrasound gel-treating system including an ultrasound gel-treating station and one or more bottles of ultrasound gel in accordance with some embodiments.

Figure 2:
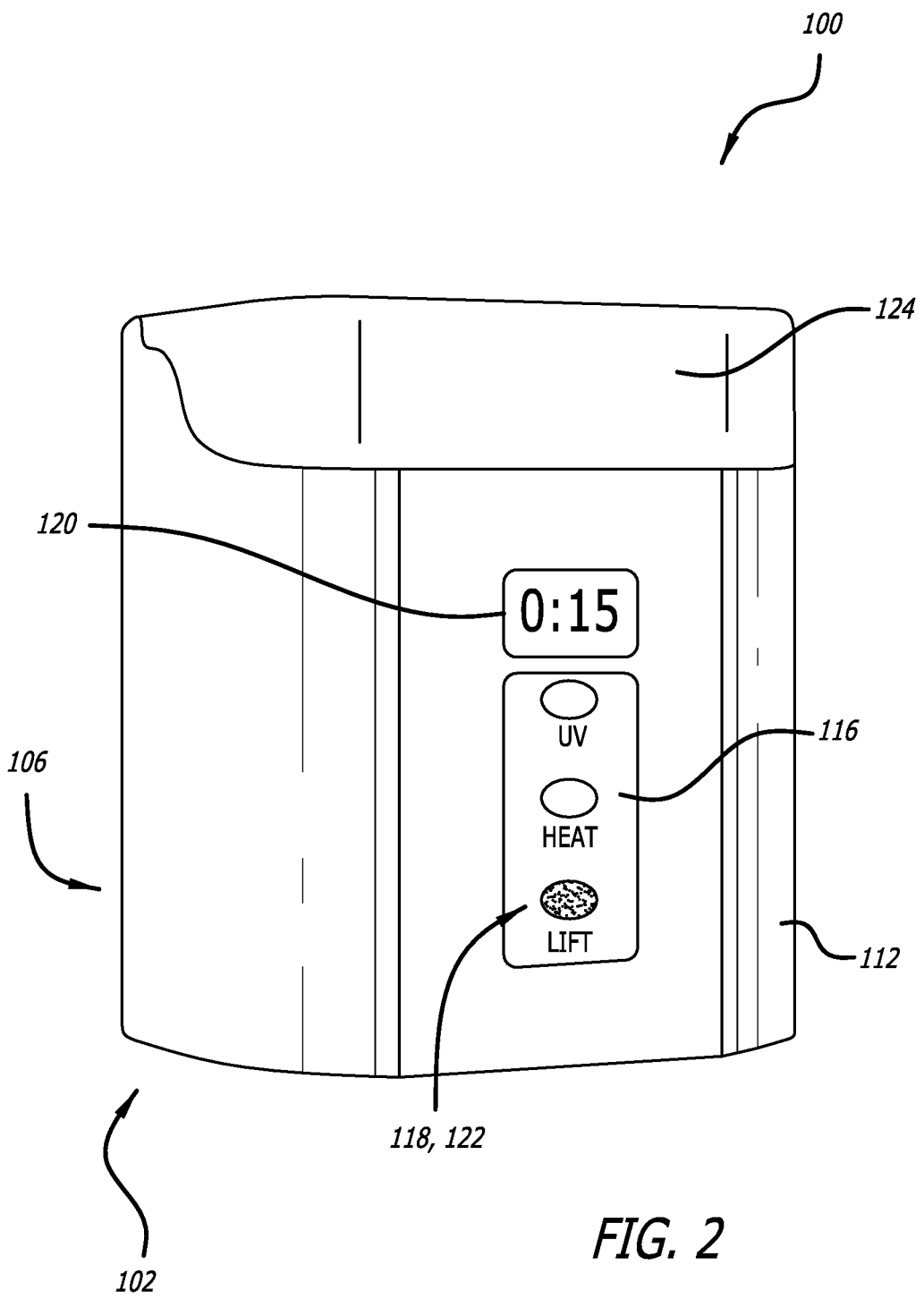

FIG. 2 further illustrates the ultrasound gel-treating system in accordance with some embodiments.

Figure 3:
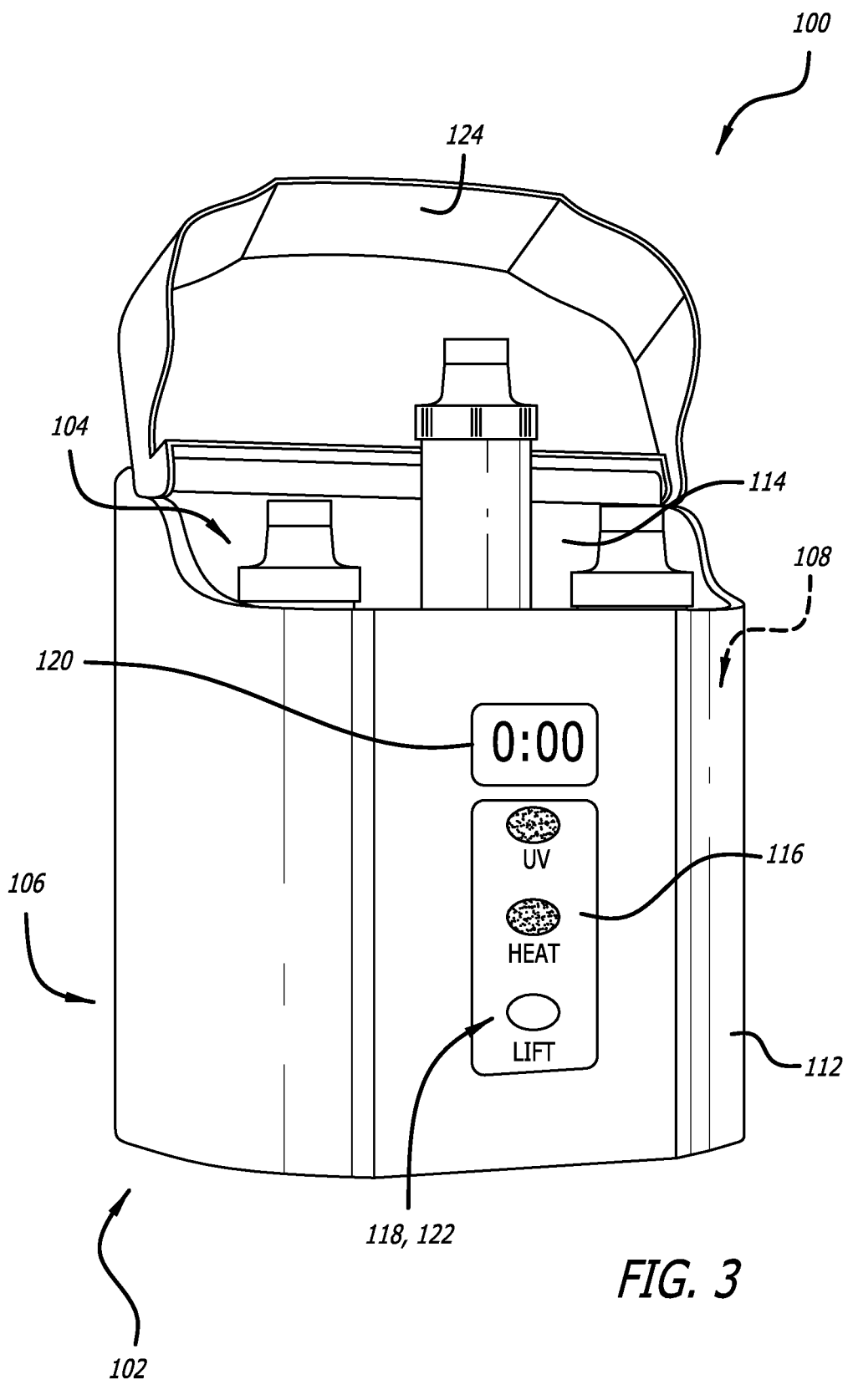

FIG. 3 further illustrates the ultrasound gel-treating system in accordance with some embodiments.

Figure 4:
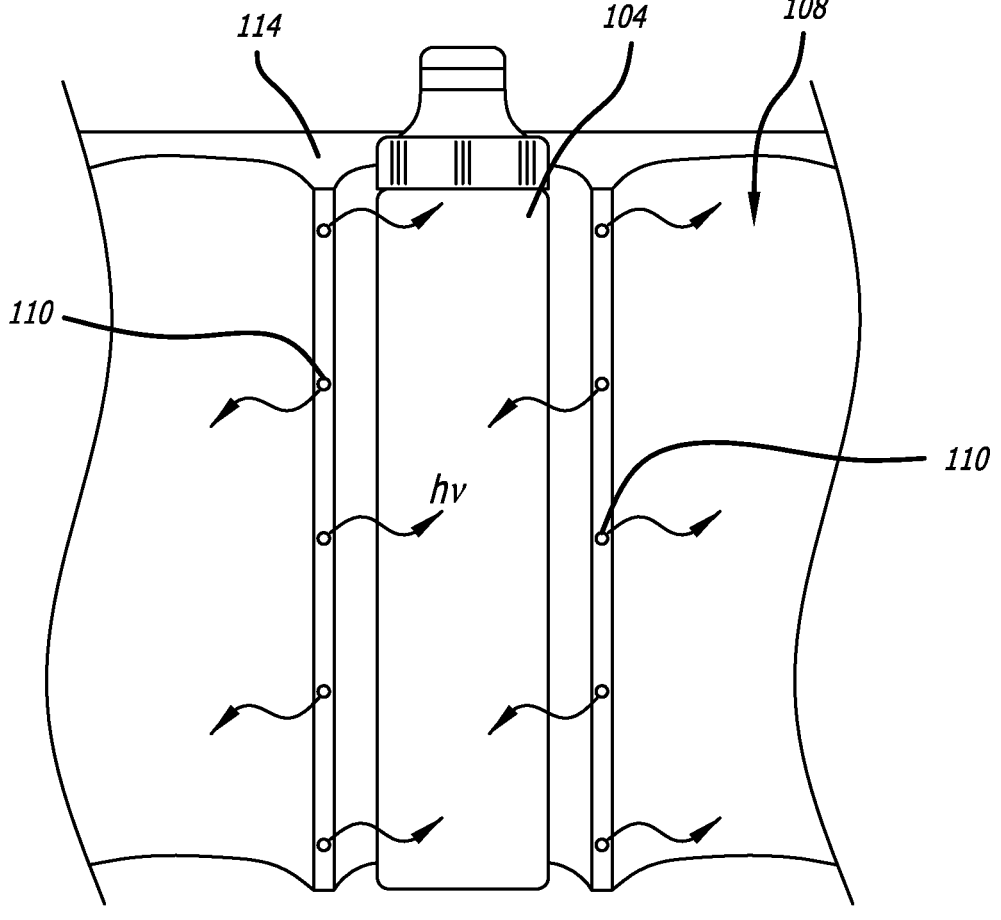

FIG. 4 illustrates irradiation of a bottle of ultrasound gel disposed in a cavity of the ultrasound gel-treating station in accordance with some embodiments.

Figure 5:
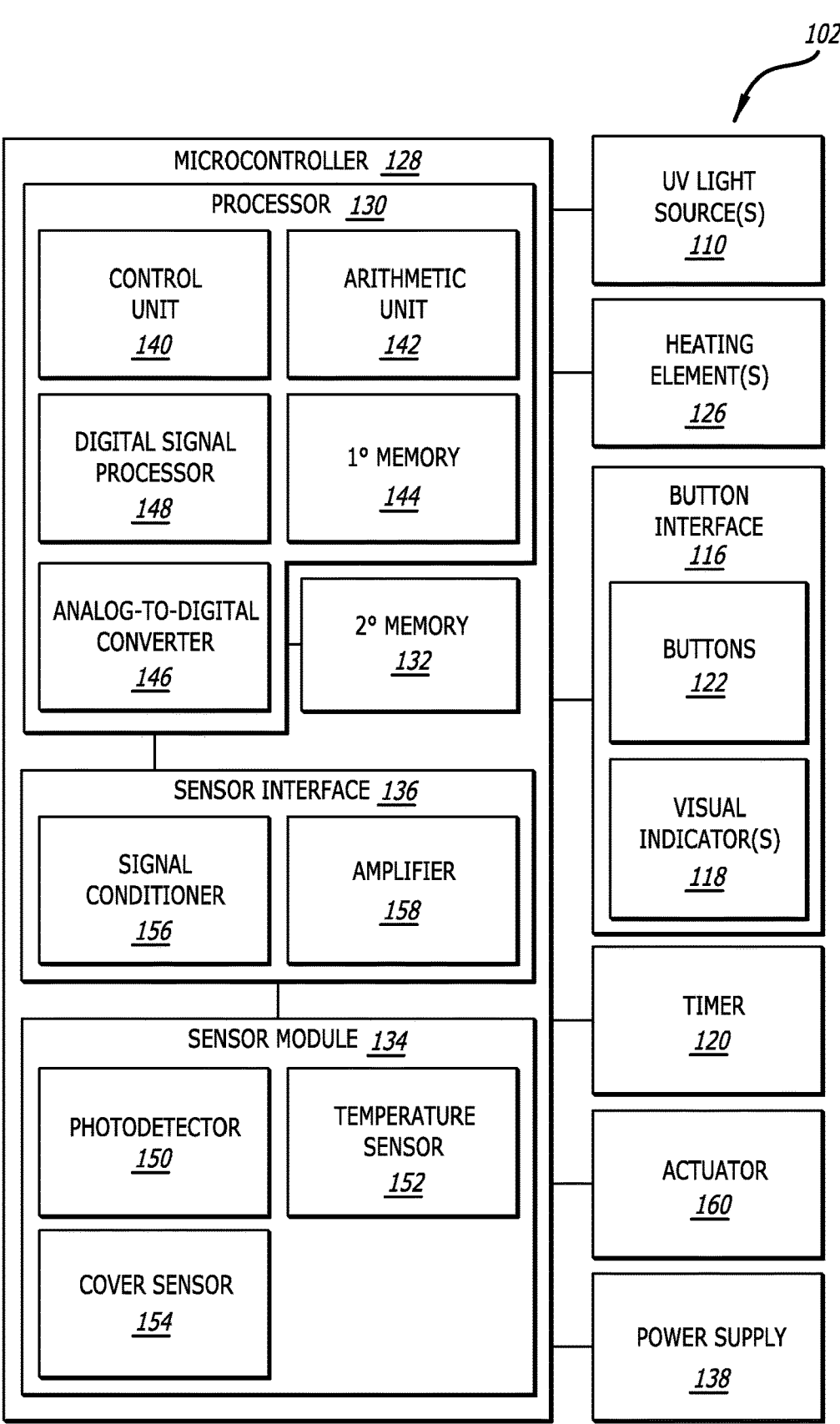

FIG. 5 provides a block diagram of the ultrasound gel-treating station in accordance with some embodiments.

DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. In addition, any of the foregoing features or steps can, in turn, further include one or more features or steps unless indicated otherwise. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

Unless defined otherwise, all technical and scientific terms used herein have the same meaning as commonly understood by those of ordinary skill in the art.

As set forth above, ultrasound gel warmers exist, but existing ultrasound gel warmers can promote bacterial growth and, therefore, be a source of infection. As such, it is not advisable to use the existing ultrasound gel warmers in sterile procedures such as those for placing percutaneous catheters. Use of packets of sterile ultrasound gel, which packets can be warmed in ultrasound gel warmers configured therefor, offer a workaround for providing warm, sterile ultrasound gel for the foregoing sterile procedures, but the packets of sterile ultrasound gel are not as economical as bottles of ultrasound gel. That, and the packets of sterile ultrasound gel produce more waste than the bottles of ultrasound gel.

Disclosed herein are ultrasound gel-treating stations, systems, and methods that address the foregoing.

Ultrasound Gel-Treating Systems

FIGS. 1-3 illustrate an ultrasound gel-treating system 100 including an ultrasound gel-treating station 102 and one or more bottles of ultrasound gel 104 in accordance with some embodiments.

As shown in FIGS. 1 and 3, the ultrasound gel-treating system 100 can include the ultrasound gel-treating station 102, the one-or-more bottles of ultrasound gel 104, or both the ultrasound gel-treating station 102 and the one-or-more bottles of ultrasound gel 104. However, it should be understood that the ultrasound gel-treating system 100 is not limited thereto.

The ultrasound gel-treating station 102 includes a housing 106, a cavity 108 within the housing 106, and one or more UV-light sources 110 disposed in the cavity 108 or the housing 106. Notably, the ultrasound gel-treating station 102 can be a stand-alone unit in which the housing 106 can be considered its body. In other embodiments, the ultrasound gel-treating station 102 is instead integrated into a roll stand or cart.

The housing 106 can include an external housing 112 and an internal housing 114. At least a portion of the external housing 112 faces outward from the ultrasound gel-treating station 102, and at least a portion of the internal housing 114 faces inward to the ultrasound gel-treating station 102. While the external housing 112 and the internal housing 114 can be separate pieces coextensive with their namesakes, each portion of housing of the external housing 112 and the internal housing 114 can be independently formed of one or more pieces. Alternatively, the external housing 112 and the internal housing 114 are an integral piece, wherein access to an internal space between walls of the external housing 112 and the internal housing 114 is, for example, through a bottom of the housing 106.

As shown in FIG. 1, the external housing 112 can include a button interface 116, one or more visual indicators 118, a timer 120, or a combination thereof. The button interface 116 can be disposed in the external housing 112, and the button interface 116 can include one or more buttons 122. The one-or-more visual indicators 118 can be integrated into the one-or-more buttons 122, as shown, or the one-or-more visual indicators 118 can be disposed in the external housing 112 separate from the one-or-more buttons 122. The timer 120 can be disposed in the external housing 112 proximal the button interface 116 such as above or below the button interface 116, but the timer 120 need not be limited thereto.

The cavity 108 within the housing 106, specifically, within the internal housing 114, can be configured to hold the one-or-more bottles of ultrasound gel 104. Indeed, as shown in FIG. 4, the cavity 108 can include a plurality of sleeves or silos formed from the internal housing 114 into which a plurality of the bottles of ultrasound gel 104 can be inserted. Such sleeves or silos can be advantageous in that any bottle of the plurality of bottles of ultrasound gel 104 used in a procedure can be returned to its sleeve or silo after the procedure without contaminating an adjacent bottle of the plurality of bottles of ultrasound gel 104.

As shown in FIGS. 1 and 2, the ultrasound gel-treating station 102 can include a cover 124 for covering the cavity 108 when at least the one-or-more bottles of ultrasound gel 104 are disposed in the cavity 108 and being treated. Such a cover 124 can be a hinged lid, as shown, a retractable cover (e.g., a tambour door), a mechanical diaphragm (e.g., mechanical iris), or the like for covering the cavity 108 when at least the one-or-more bottles of ultrasound gel 104 are disposed in the cavity 108 and being irradiated, warmed, or both irradiated and warmed. Notably, for user protection, the ultrasound gel-treating station 102 is configured to stop irradiating the one-or-more bottles of ultrasound gel 104 or the cavity 108, itself, when the cavity 108 is uncovered such as by lifting the hinged lid, retracting the retractable cover, opening the mechanical diaphragm, or the like. However, the ultrasound gel-treating station 102 need not stop warming the one-or-more bottles of ultrasound gel 104 or the cavity 108, itself, when the cavity 108 is uncovered; that is, unless the warming is dependent upon the heat dissipated by the one-or-more UV-light sources 110.

FIG. 4 illustrates irradiation of a bottle of ultrasound gel disposed in the cavity 108 of the ultrasound gel-treating station 102 in accordance with some embodiments.

As shown, the one-or-more UV-light sources 110 can be disposed in the cavity 108, in the housing 106, behind the housing 106, or the like, optionally, in a combination thereof, for irradiating the one-or-more bottles of ultrasound gel 104 with germicidal radiation when the one-or-more bottles of ultrasound gel 104 are disposed in the cavity 108. When the one-or-more UV-light sources 110 are disposed in the cavity 108, the one-or-more UV-light sources 110 can be wholly disposed in the cavity 108 with corresponding electrical leads passing through through holes in the internal housing 114 as well as the internal space between the walls of the external and internal housing 114 to the microcontroller 128. When the one-or-more UV-light sources 110 are disposed in the housing 106, the one-or-more UV-light sources 110 can be partially disposed in the cavity 108 (e.g., peaking into the cavity 108) with a remainder of the one-or-more UV-light sources 110 disposed in the through holes of the internal housing 114, the corresponding electrical leads passing through the internal space between the walls of the external and internal housing 112 and 114 to the microcontroller 128. Lastly, when the one-or-more UV-light sources 110 are behind the housing 106, the one-or-more UV-light sources 110 can be mounted in the internal space between the walls of the external and internal housing 112 and 114 such that the one-or-more UV-light sources 110 emit the germicidal radiation toward the cavity 108, at least the internal housing 114 around the cavity 108 being a polymeric material sufficiently transparent to transmit UV light therethrough, optionally, a rigid formulation of the pliable polymeric material set forth below. As in other embodiments, the corresponding electrical leads of the one-or-more UV-light sources 110 pass through the internal space between the walls of the external and internal housing 112 and 114 to the microcontroller 128.

The one-or-more UV-light sources 110 can be independently selected from a low-pressure mercury lamp, an excimer lamp, a pulsed xenon lamp, and a semiconductor light source, the semiconductor light source, in turn, selected from a light-emitting diode ("LED"), a laser, and a superluminescent diode ("SLD"), which SLD, notably, combines high-power and brightness characteristics of lasers with low-power characteristic of LEDs. By way of example, FIG. 4 shows a plurality of LEDs disposed in the internal housing 114 and emitting the germicidal radiation into the cavity 108. Such germicidal radiation emitted by the one-or-more UV-light sources 110 can be selected from broad spectrum UV-visible light, broad spectrum UV light, UVA light, UVB light, UVC light, blue light, and modulated light thereof, wherein the modulated light is modulated with respect to wavelength or frequency, power, including ramping the power, duration, including pulse durations when pulsing the modulated light, or a combination thereof.

Notably, heat dissipated by the one-or-more UV-light sources 110 can warm the one-or-more bottles of ultrasound gel 104 when the one-or-more bottles of ultrasound gel 104 are disposed in the cavity 108. Notwithstanding the foregoing, the ultrasound gel-treating station 102 can further include one or more heating elements 126 for warming the one-or-more bottles of ultrasound gel 104 when the one-or-more bottles of ultrasound gel 104 are disposed in the cavity 108.

The one-or-more heating elements 126 can be disposed in the cavity 108, in the housing 106, behind the housing 106, or the like, optionally, in a combination thereof, for warming the one-or-more bottles of ultrasound gel 104 when the one-or-more bottles of ultrasound gel 104 are disposed in the cavity 108. When the one-or-more heating elements 126 are disposed in the cavity 108, the one-or-more heating elements 126 can be wholly disposed in the cavity 108 with corresponding electrical leads passing through through holes in the internal housing 114 as well as the internal space between the walls of the external and internal housing 112 and 114 to the microcontroller 128. When the one-or-more heating elements 126 are disposed in the housing 106, the one-or-more heating elements 126 can be partially disposed in the cavity 108 (e.g., peaking into the cavity 108) with a remainder of the one-or-more heating elements 126 disposed in the through holes of the internal housing 114, the corresponding electrical leads passing through the internal space between the walls of the external and internal housing 112 and 114 to the microcontroller 128. Lastly, when the one-or-more heating elements 126 are behind the housing 106, the one-or-more heating elements 126 can be mounted in the internal space between the walls of the external and internal housing 112 and 114 such that the one-or-more heating elements 126 emit infrared radiation toward the cavity 108. As in other embodiments, the corresponding electrical leads of the one-or-more heating elements 126 pass through the internal space between the walls of the external and internal housing 112 and 114 to the microcontroller 128.

Notably, when both the one-or-more UV-light sources 110 and the one-or-more heating elements 126 are present, the one-or-more UV-light sources 110 and the one-or-more heating elements 126 can independently adopt any configuration set forth above with respect to being disposed in the cavity 108, in the housing 106, behind the housing 106, or the like.

FIG. 5 provides a block diagram of the ultrasound gel-treating station 102 including a microcontroller 128 in accordance with some embodiments.

As shown, the ultrasound gel-treating station 102 can further include the microcontroller 128 configured for operating the ultrasound gel-treating station 102. The microcontroller 128 can be disposed within the housing 106 such as the internal space between the walls of the external and internal housing 112 and 114.

The microcontroller 128 can include components selected from at least a processor 130, secondary memory 132, a sensor module 134, a sensor interface 136, and a power supply 138 such as an internal power supply (e.g., a battery) or an external power supply (e.g., utility power). The processor 130 can include a control unit 140, an arithmetic unit 142, and primary memory 144 (e.g., cache memory, RAM, or both), wherein the primary memory 144 can be configured to store in-use programs and data (e.g., the sensor data). While the primary memory 144 can be within the same package as a remainder of the processor 130 as alluded to in FIG. 5, at least the foregoing RAM can be distributed outside the package of the processor 130, for example, in its own package.

The secondary memory 132 can be configured to store data and programs including instructions, logic, algorithms including machine-learning algorithms, artificial intelligence ("AI") models, or some combination thereof for loading into the primary memory 144 for use by the processor 130, for example, when determining from, for example, the sensor data, whether the one-or-more bottles of ultrasound gel 104 need to be disinfected, warmed, or both disinfected and warmed, whether the one-or-more bottles of ultrasound gel 104 are being irradiated, warmed, or both irradiated and warmed, how much longer the one-or-more bottles of ultrasound gel 104 should be irradiated, warmed, or both irradiated and warmed, whether the one-or-more bottles of ultrasound gel 104 have been disinfected, warmed, or both disinfected and warmed, or some combination thereof. Should the microcontroller 128 include the sensor module 134 and the sensor interface 136 to sense conditions in the cavity 108 for starting, stopping, or adjusting the one-or-more UV-light sources 110, the one-or-more heating elements 126, or both the one-or-more UV-light sources 110 and the one-or-more heating elements 126 in accordance with the foregoing, the processor 130 can further include an analog-to-digital converter 146 ("ADC") configured to convert electrical signals from the one-or-more sensors from analog to digital and a digital-signal processor 148 ("DSP") configured to generate sensor data from the electrical signals. While the ADC and DSP 146 and 148 can be within the same package as a remainder of the processor 130 as alluded to in FIG. 5, the ADC and DSP 146 and 148 can be distributed outside the package of the processor 130, for example, in their own package.

When present, the sensor module 134 can include one or more sensors selected from at least a photodetector 150, a temperature sensor 152, and a cover sensor 154 configured to generate electrical signals in response to photons detected, temperature sensed, and cover-state sensed, respectively, wherein the cover-state sensed can be, for example, open cover, ajar cover, or closed cover. Further, when present, the sensor interface 136 can include a signal conditioner 156 configured to standardize the electrical signals through voltage or current limiting, anti-aliasing filtering, or the like. In addition, the sensor interface 136 can include an amplifier 158 configured to amplify the electrical signals and, thereby, increase their signal-to-noise ratio. Again, the ADC 146 can be configured to convert the electrical signals from analog to digital, and the DSP 148 can be configured to generate the sensor data from the electrical signals for determining whether to start, stop, or adjust the one-or-more UV-light sources 110, the one-or-more heating elements 126, or both the one-or-more UV-light sources 110 and the one-or-more heating elements 126 in accordance with the sensor data.

The microcontroller 128 can be coupled to the one-or-more visual indicators 118 disposed in the housing 106 for indicating the one or more bottle of ultrasound gel need to be disinfected, warmed, or both disinfected and warmed, the one-or-more bottles of ultrasound gel 104 are being irradiated, warmed, or both irradiated and warmed, or the one-or-more bottles of ultrasound gel 104 have been disinfected, warmed, or both disinfected and warmed. Indeed, the one-or-more visual indicators 118 can be integrated into the one-or-more buttons 122 as LEDs behind the one-or-more buttons 122, the LEDs having different colors (e.g., red, yellow, and green) of light to indicate the one or more bottle of ultrasound gel need to be disinfected, warmed, or both disinfected and warmed (e.g., red light), the one-or-more bottles of ultrasound gel 104 are being irradiated, warmed, or both irradiated and warmed (e.g., yellow light), or the one-or-more bottles of ultrasound gel 104 have been disinfected, warmed, or both disinfected and warmed (e.g., green light). Additionally or alternatively, the microcontroller 128 can be coupled to the timer 120 disposed in the external housing 112 for indicating, for example, by a countdown, when the one-or-more bottles of ultrasound gel 104 will be disinfected, warmed, or both disinfected and warmed.

The ultrasound gel-treating station 102 can further include an actuator 160 disposed in the housing 106 for lifting the one-or-more bottles of ultrasound gel 104 at least partially out of the ultrasound gel-treating station 102 so any bottle of the one-or-more bottles of ultrasound gel 104 can be grabbed without touching a potentially contaminated exterior surface of the ultrasound gel-treating station 102. The actuator 160 can be coupled to one or more movable bottoms of the plurality of sleeves or silos of the internal housing 114 set forth above for lifting the one-or-more bottles of ultrasound gel 104 at least partially out of the ultrasound gel-treating station 102.

As to the one-or-more bottles of ultrasound gel 104, each bottle of the one-or-more bottles of ultrasound gel 104 can be formed of a pliable polymeric material sufficiently transparent to transmit UV light therethrough. Such a polymeric material can be selected from a polycarbonate, a polyethylene terephthalate, a polyvinyl chloride, a polyurethane, a poly (methyl methacrylate), a polyimide, a polyetherimide, and a cyclic olefin polymer, the polymeric material optionally including one or more comonomer residues, thereby making the foregoing polymeric material a copolymer, one or more plasticizers, or a combination thereof.

Methods

Methods include methods of the ultrasound gel-treating system or station 100 or 102, itself, as well as methods of using the ultrasound gel-treating system 100.

A method of the ultrasound gel-treating station 102 can include at least a sensing operation of sensing conditions in the cavity 108 and a determining operation of determining whether the one-or-more UV-light sources 110, the one-or-more heating elements 126, or both the one-or-more UV-light sources 110 and the one-or-more heating elements 126 should be started, stopped, or adjusted. Further, the method of the ultrasound gel-treating station 102 can include an indicating operation of indicating with the one-or-more visual indicators 118 the one-or-more bottles of ultrasound gel 104 need to be disinfected, warmed, or both disinfected and warmed, the one-or-more bottles of ultrasound gel 104 are being irradiated, warmed, or both irradiated and warmed, or the one-or-more bottles of ultrasound gel 104 have been disinfected, warmed, or both disinfected and warmed. Such operations of the ultrasound gel-treating station 102 and others can be further understood from disclosure set forth above.

A method of using the ultrasound gel-treating station 102 can include at least a witnessing operation of witnessing the ultrasound gel-treating station 102 indicating with the one-or-more visual indicators 118 that the plurality of bottles of ultrasound gel 104 have been disinfected, warmed, or both disinfected and warmed. Further, the method of using the ultrasound gel-treating station 102 can include an uncovering operation of uncovering the cavity 108, a waiting operation of waiting for the actuator 160 to lift the plurality of bottles of ultrasound gel 104 at least partially out of the ultrasound gel-treating station 102, and a grabbing operation of grabbing a bottle of the plurality of bottles of ultrasound gel 104 without touching a potentially contaminated exterior surface of the ultrasound gel-treating station 102. Further yet, the method of using the ultrasound gel-treating station 102 can include returning the bottle to its sleeve or silo without contaminating any other bottle of the plurality of bottles of ultrasound gel 104.

While some particular embodiments have been disclosed herein, and while the particular embodiments have been disclosed in some detail, it is not the intention for the particular embodiments to limit the scope of the concepts provided herein. Additional adaptations or modifications can appear to those of ordinary skill in the art, and, in broader aspects, these adaptations or modifications are encompassed as well. Accordingly, departures may be made from the particular embodiments disclosed herein without departing from the scope of the concepts provided herein.

What is claimed is:

1. An ultrasound gel-treating station, comprising:
a housing;
a cavity within the housing configured to hold one or more bottles of ultrasound gel;
one or more heating elements disposed in the cavity or the housing about the cavity for warming one or more bottles of ultrasound gel when the one or more bottles of ultrasound gel are disposed in the cavity;
and one or more ultraviolet ("UV")-light sources disposed in the cavity or the housing about the cavity for irradiating the one or more bottles of ultrasound gel with germicidal radiation configured to disinfect without causing damage to the one or more bottles of ultrasound gel when the one or more bottles of ultrasound gel are disposed in the cavity.

2. The ultrasound gel-treating station of claim 1, further comprising a cover for covering the cavity when at least the one or more bottles of ultrasound gel are disposed in the cavity and being warmed, irradiated, or both warmed and irradiated.

3. The ultrasound gel-treating station of claim 2, wherein the ultrasound gel-treating station is configured to stop irradiating the one or more bottles of ultrasound gel when the cavity is uncovered.

4. The ultrasound gel-treating station of claim 1, further comprising a microcontroller configured for operating the ultrasound gel-treating station, the microcontroller disposed within the housing with a sensor module including one or more sensors configured to sense conditions in the cavity for starting, stopping, or adjusting the one or more heating elements or the one or more UV-light sources.

5. The ultrasound gel-treating station of claim 4, wherein the microcontroller is further coupled to one or more visual indicators disposed in the housing for indicating when the one or more bottles of ultrasound gel are being warmed, irradiated, both warmed and irradiated, or subsequent thereto.

6. The ultrasound gel-treating station of claim 4, wherein the microcontroller is further coupled to a timer disposed in the housing for indicating when the one or more bottles of ultrasound gel will be warm, disinfected, or both warmed and disinfected.

7. The ultrasound gel-treating station of claim 1, further comprising an actuator disposed in the housing for lifting the one or more bottles of ultrasound gel at least partially out of the ultrasound gel-treating station.

8. The ultrasound gel-treating station of claim 1, wherein the ultrasound gel-treating station is integrated into a roll stand or cart.

9. An ultrasound gel-treating station, comprising:
a housing;
a cavity within the housing configured to hold the one or more bottles of ultrasound gel;
one or more ultraviolet ("UV")-light sources disposed in the cavity or the housing about the cavity for irradiating the one or more bottles of ultrasound gel with germicidal radiation configured to disinfect without causing damage to the one or more bottles of ultrasound gel when the one or more bottles of ultrasound gel are disposed in the cavity.

10. The ultrasound gel-treating station of claim 9, wherein heat dissipated by the one or more UV-light sources warms the one or more bottles of ultrasound gel when the one or more bottles of ultrasound gel are disposed in the cavity.

11. The ultrasound gel-treating station of claim 9, further comprising a cover for covering the cavity when at least the one or more bottles of ultrasound gel are disposed in the cavity and being irradiated.

12. The ultrasound gel-treating station of claim 11, wherein the ultrasound gel-treating station is configured to stop irradiating the one or more bottles of ultrasound gel when the cavity is uncovered.

13. The ultrasound gel-treating station of claim 9, further comprising a microcontroller configured for operating the ultrasound gel-treating station, the microcontroller disposed within the housing with a sensor module including one or more sensors configured to sense conditions in the cavity for starting, stopping, or adjusting the one or more UV-light sources.

14. The ultrasound gel-treating station of claim 13, wherein the microcontroller is further coupled to one or more visual indicators disposed in the housing for indicating when the one or more bottles of ultrasound gel are being irradiated.

15. The ultrasound gel-treating station of claim 13, wherein the microcontroller is further coupled to a timer disposed in the housing for indicating when the one or more bottles of ultrasound gel will be disinfected.

16. The ultrasound gel-treating station of claim 9, further comprising an actuator disposed in the housing for lifting the one or more bottles of ultrasound gel at least partially out of the ultrasound gel-treating station.

17. An ultrasound gel-treating system, comprising:

one or more bottles of ultrasound gel, each bottle of the one or more bottles formed of a pliable polymeric material sufficiently transparent to transmit ultraviolet ("UV") light therethrough; and an ultrasound gel-treating station including:

a housing;

a cavity within the housing configured to hold the one or more bottles of ultrasound gel; and one or more ultraviolet ("UV")-light sources disposed in the cavity or the housing about the cavity for irradiating the one or more bottles of ultrasound gel with germicidal radiation configured to disinfect without causing damage to the one or more bottles of ultrasound gel when the one or more bottles of ultrasound gel are disposed in the cavity.

18. The ultrasound gel-treating system of claim 17, the ultrasound gel-treating station further comprising one or more heating elements disposed in the cavity or the housing about the cavity for warming the one or more bottles of ultrasound gel when the one or more bottles of ultrasound gel are disposed in the cavity.

19. The ultrasound gel-treating system of claim 17, wherein heat dissipated by the one or more UV-light sources warms the one or more bottles of ultrasound gel when the one or more bottles of ultrasound gel are disposed in the cavity.

20. The ultrasound gel-treating system of claim 17, the ultrasound gel-treating station further comprising a cover for covering the cavity when at least the one or more bottles of ultrasound gel are disposed in the cavity and being irradiated.

21. The ultrasound gel-treating system of claim 17, wherein the ultrasound gel-treating station is configured to stop irradiating the one or more bottles of ultrasound gel when the cavity is uncovered.

22. The ultrasound gel-treating system of claim 17, the ultrasound gel-treating station further comprising a microcontroller configured for operating the ultrasound gel-treating station, the microcontroller disposed within the housing with a sensor module including one or more sensors configured to sense conditions in the cavity for starting, stopping, or adjusting the one or more UV-light sources.

23. The ultrasound gel-treating system of claim 17, the ultrasound gel-treating station further comprising an actuator disposed in the housing for lifting the one or more bottles of ultrasound gel at least partially out of the ultrasound gel-treating station.

24. The ultrasound gel-treating system of claim 17, wherein the germicidal radiation is selected from broad spectrum UV-visible light, broad spectrum UV light, UVA light, UVB light, UVC light, blue light, and modulated light thereof, wherein the modulated light is modulated with respect to frequency, power, duration, or a combination thereof.

25. The ultrasound gel-treating system of claim 17, wherein the pliable polymeric material of which the one or more bottles are formed is selected from a polycarbonate, a polyethylene terephthalate, a polyvinyl chloride, a polyurethane, a poly (methyl methacrylate), a polyimide, a polyetherimide, and a cyclic olefin polymer, the pliable polymeric material optionally including one or more comonomer residues, one or more plasticizers, or a combination thereof.

* * * * *